United States Patent [19]

Krementsov

[11] 4,207,902

[45] Jun. 17, 1980

[54] INSTRUMENT AND METHOD OF MEASURING DILATATION OF CERVIX UTERI

[76] Inventor: Yury Krementsov, 85-11 34th Ave., #2B, Jackson Heights, N.Y. 11392

[21] Appl. No.: 958,810

[22] Filed: Nov. 8, 1978

[51] Int. Cl.² .................................................. A61B 5/10
[52] U.S. Cl. ...................................... 128/778; 128/775; 33/143 C
[58] Field of Search ............... 128/778, 775, 777, 361; 33/174 D, 143 C

[56] References Cited

U.S. PATENT DOCUMENTS

| | | | |
|---|---|---|---|
| 1,953,498 | 4/1934 | Pieri et al. | 33/174 D |
| 2,241,451 | 5/1941 | Fist | 128/778 |
| 2,507,959 | 5/1950 | Chapman | 33/174 D |
| 3,097,637 | 7/1963 | Horton | 128/775 |
| 4,141,345 | 2/1979 | Allen et al. | 128/778 |

FOREIGN PATENT DOCUMENTS

Ad.11910 of 1897 United Kingdom ..................... 128/361

Primary Examiner—Kyle L. Howell
Attorney, Agent, or Firm—Ilya Zborovsky

[57] ABSTRACT

An instrument for measuring dilatation of cervix uteri has two elongated arms movable relative to one another in a scissors-like manner and each having a measuring portion and an indicating portion spaced from one another. Two expansible loops are formed at the end of the measuring portions, whereas an indicating tip is provided at the end of one indicating portion and a scale is provided at the end of the other indicating portion. In accordance with the inventive method, fingers of a physician extend through the loops so as to palpate the edge of the orifice of cervix uteri and move the loops apart from one another. At the same time, the indicating tip points to a respective graduation mark of the scale and thereby shows a degree of dilation.

12 Claims, 4 Drawing Figures

4,207,902

INSTRUMENT AND METHOD OF MEASURING DILATATION OF CERVIX UTERI

BACKGROUND OF THE INVENTION

The present invention relates to an instrument for and method of measuring dilatation of cervix uteri during a first stage of labor.

In medical practice a degree of dilatation of cervix uteri is measured by fingers of a physician. A physician inserts two fingers into a birth canal so that his or her fingers reach the edges of the orifice of cervix uteri, palpates the cervix uteri by one finger when the former is dilated to a small degree, and moves the fingers apart from one another so as to bring them into contact with the edge of the orifice with the dilated cervix uteri. The thickness of the one finger in the first step and the distance between the fingers in the second step are evaluated by a physician on the ground of his or her sensing and serve as indications of the degree of dilatation of cervix uteri.

It is to be understood that such measurements cannot be accurate. The same degree of dilatation is evaluated by various physicians differently, and the thus-obtained results are not identical. For this reason such measurements are proved to be misleading in many cases, since a physician cannot know exactly his or her finger thickness and a distance therebetween in an extended position when the fingers are moved apart from one another. However, accurate determination of the degree of dilatation of cervix uteri is of an extreme importance for successful monitoring of progress and therefore outcome of the labor.

SUMMARY OF THE INVENTION

Accordingly, it is an object of the present invention to provide an instrument for and a method of measuring dilatation of cervix uteri, which avoid the disadvantages of the prior art.

More particularly, it is an object of the present invention to provide an instrument for and a method of measuring dilatation of cervix uteri, which provide for more accurate measurements.

In keeping with these objects and with others which will become apparent hereinafter, one feature of the present invention resides, briefly stated, in an instrument which has two arms connected with one another in a scissors-like manner and having two measuring portions provided with differently spaced loops for inserting physician's fingers and two indicating portions provided with a scale and an indicating tip, wherein the loops are expansible and the arms are movable between the initial position in which the loops are coaxial and one finger can extend through simultaneously two loops so as to palpate the edge of the orifice of cervix uteri, and a plurality of further positions in which two fingers can be inserted and extend beyond the loops which are spaced from one another to palpate the edge by two fingers. In such a construction a physician palpates the edge of the orifice of the cervix uteri by his or her fingers and correspondingly moves the loops into contact with the same, whereas the indicating tip of one indicating portion points to a respective graduation mark of the scale and thereby indicates a degree of dilatation of cervix uteri. This assures significantly more correct measurements of dilatation. The expansible loops permit insertion of the fingers of physicians, the fingers having differing thicknesses.

The novel features which are considered as characteristic for the present invention are set forth in particular in the appended claims. The invention itself, however, both as to its construction and its method of operation, together with additional objects and advantages thereof, as well as a new method of measuring in accordance with the invention, will be best understood from the following specification and description of specific embodiments when read in connection with the accompanying drawing.

DESCRIPTION OF PREFERRED EMBODIMENTS

Figure 4:
FIG. 4 is a view showing loops which are provided on measuring portions of the instrument, in an enlarged scale.

An inventive instrument for measuring dilatation of cervix uteri has two arms which are identified in toto by reference numerals 1 and 2. The arm 1 has a measuring portion 3 and an indicating portion 7, whereas the arm 2 has a measuring portion 4 and an indicating portion 8. The arms 1 and 2 have also central portions 5 and 6, respectively, each located between a respective one of the measuring and indicating portions. The arms 1 and 2 are connected with one another in the region of their central portions 5 an 6 so as to perform a scissors-like movement. The connection may be formed by a screw 11 which is known per se in the art.

The indicating portion 8 of the arm 2 is formed by a sector with rounded edges which is provided with a scale including a plurality of graduation marks. The indicating portion 7 of the arm 1 is formed by an indicating tip adapted to point to the graduation marks of the scale. The rounded edges of the sector prevent injury of both a physician and a patient.

Figure 3:
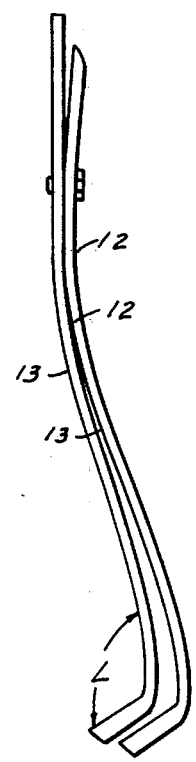
FIG. 3 is a side view of the instrument in the position shown in FIG. 1.

As can be seen particularly from FIG. 3, the measuring portions 3 and 4 of the arms are curved in a direction which is transverse to the direction of elongation. The curvature of these portions is so selected as to correspond to the curvature of a physician's palm when his or her fingers are inserted in the birth canal to perform measurements. The arms 1 and 2 have lower surfaces 13 which are flat so as to provide smooth abutment of the instrument against the physician's palm. On the other hand, the arms 1 and 2 are formed by flat members which also have flat upper surfaces so as to prevent injury of a patient by the instrument.

The measuring portions 3 and 4 of the arms have ends which are spaced from the respective central portions 5 and 6 and are provided with loops 9 and 10, respectively. The loop 9 is spaced from the central portions or from the screw 11 by a distance which is greater than the distance by which the loops 10 is spaced from the same. In such a construction, when measuring portions 3 and 4 of the arms in an initial position approach one another, the loops 10 and 9 are located one after the other and they are coaxial with each other. The loops are flattened.

Figure 1:
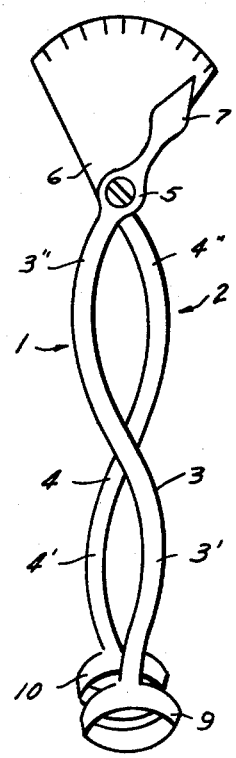
FIG. 1 is a front view of an instrument in accordance with the present invention, in a proximal position of its arms.
Figure 2:
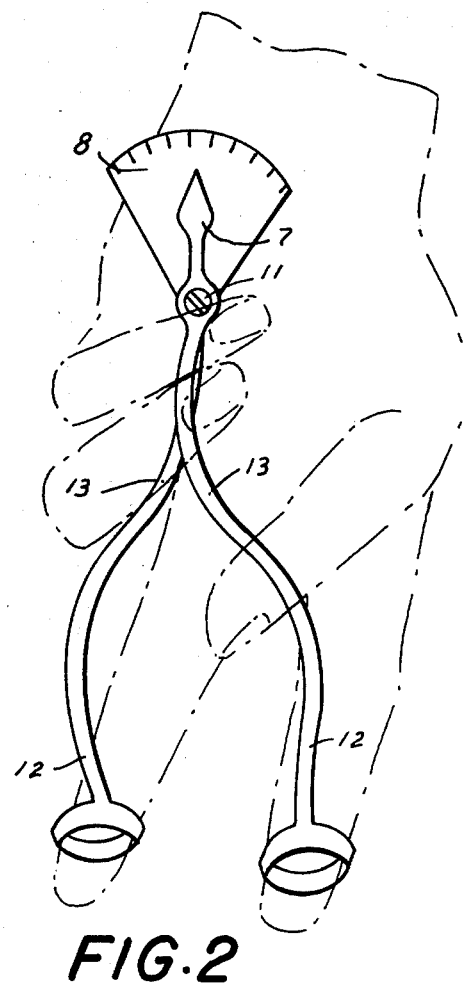
FIG. 2 is a view corresponding to the view shown in FIG. 1 but illustrating the instrument in a distal position of its arm.

As can be seen particularly from FIG. 1, the measuring portions 3 and 4 have sections 3' and 4' located adjacent to the loops 9 and 10, and sections 3" and 4" located adjacent to the central portions 5 and 6, respectively. The measuring portions 3 and 4 are further so curved that the sections 3' and 3" of the measuring portion 3 are located at opposite sides of a longitudinal axis of the instrument. The same is true with respect to the sections 4' and 4" of the measuring portion 4. On the other hand, the section 3' is located opposite to the section 4', whereas the section 3" is located opposite to the section 4". In such a construction when the arms are moved apart from one another and located in a distal position shown in FIG. 2, they occupy a smaller space in a transverse direction than straight arms would occupy.

A method of measuring in accordance with the present invention is performed with the use of the above-described instrument in the following manner.

The arms 1 and 2 are moved toward one another to the initial or proximal position which is shown in FIG. 1. In this position the loops are located one after the other and coaxial with each other. The loops are expansible, for example, they may be constructed of an expansible material, or may be constructed of a springy material and slit as shown in FIG. 4. Preferably, the loops have a diameter equal to substantially 1.2 cm which corresponds to the smallest thickness of a second and third finger of a physician's hand. A synthetic plastic material may be utilized as an expansible material, and metal can be utilized as springy material of the loops.

When the loops 9 and 10 are in the above-mentioned proximal position, the physician puts his or her one finger of hand simultaneously into two loops in the coaxial position of the latter, and introduces the instrument into the birth canal. The finger is so inserted into the loops that it extends outwardly beyond the latter. The thus-extended finger palpates the edge of the orifice of cervix uteri in an initial stage of dilatation. If the one finger and thereby the loops 9 and 10 in the coaxial position contact the edge, the indicating tip 7 will point to the graduation mark corresponding to 1.2 cm.

During further dilatation of cervix uteri, the measuring portions 3 and 4 are moved apart from one another until the two physcians fingers inserted into two spaced loops (FIG. 2) palpate the edge of the dilated cervix uteri, since the fingers extend outwardly beyond the loops. The loops 9 and 10 are brought into contact with the edges by such movement, and the indicating tip 7 points to a respective one of the graduation marks which corresponds to an instant degree of dilatation of cervix uteri. The loops 9 and 10 are conical in correspondence with the conical shape of the second and third hand fingers. Other fingers hold the instrument.

Thus, on the one hand a physician can palpate the edge of the cervix uteri by his or her hand fingers, and, on the other, hand, the accurate results appear on the scale of the instrument. Since the loops are expansible, the second and third fingers of various physicians having differing thicknesses can be inserted into and extend outwardly beyond the loops so as to palpate the edges of the orifice of cervix uteri. It should further be noted that the indicating tip 7 and scale are provided on the upper surfaces of the arms which face away from the physician palm in operational position, whereas the loops extend from the lower surface of the arm in a direction away from the latter and at a certain angle relative to the arms.

It will be understood that each of the elements described above may also find a useful application in other types of construction. The invention is not intended to be limited to the details shown, since various modifications may be made without departing from the spirit of the present invention.

What is claimed as new and desired to be protected by Letters Patent is set forth in particular in the appended claims:

1. An instrument for measuring dilatation of cervix uteri during a first stage of labor, comprising
   a first and a second elongated arm each having a central portion, a measuring portion extending from said central portion in a first direction, and an indicating portion extending from said central portion in a second direction which is opposite to said first direction, each of said arms having an end which is spaced from a respective one of said central portions, one of said measuring portions being longer than the other portion;
   two loops each having an axis and located at the end of a respective measuring portion and thereby at differing distances from a respective central portion, each of said loops being expansible so that fingers of differing thicknesses can be inserted therein;
   a scale located at the end of one indicating portion and having a plurality of graduation marks corresponding to different degrees of dilatation of cervix uteri;
   an indicating tip provided at the end of the other indicating portion and arranged to point to said graduation marks of said scale; and
   means for connecting said arms in the region of said central portion so that said arms move relative to one another in a scissors-like manner between a proximal position in which said loops are located one after the other and their axes substantially coincide so that one finger of a user can be inserted simultaneously into two loops and extend outwardly beyond the same so as to palpate the edge of the orifice of cervix uteri, and a plurality of distal positions in which said loops are spaced from one another and two fingers of the user can be inserted separately into said loops and extend outwardly beyond the same so as to palpate the edge of the orifice by two fingers and to thereby determine by which distance said loops must be withdrawn from one another, said indicating tip in each of said positions pointing to a respective graduation marks of said scale and thereby showing a degree of dilatation.

2. An instrument as defined in claim 1, wherein said loops have an inner diameter corresponding to a minimum diameter of a second and third fingers and is equal to substantially 1.2 cm.

3. An instrument as defined in claim 1, wherein said arms have lower surfaces arranged to lie on a user's palm and facing in a direction which is transverse to the direction of elongation of said arms, an upper surfaces facing in said transverse direction and spaced from said lower surfaces, said scale being provided on the upper surface of the indicating portion of one arm, said loops being provided on the lower surfaces of said measuring portions and extending in said transverse direction away from the latter.

4. An instrument as defined in claim 3, wherein said arms are flat, said upper surfaces of said arms being flat so as to provide for matching to the user's palm, said upper surfaces of said arms being also flat so as to prevent injury of a patient by said arms.

5. An instrument as defined in claim 3, wherein said measuring portions are curved in said transverse direction and have a curvature which corresponds to that of a user's palm when the fingers are inserted in a curved birth canal.

6. An instrument as defined in claim 1, wherein the instrument has a longitudinal axis which in said proximal position coincides with the axes of said loops, each of said measuring portions having a first section located adjacent to a respective loop, and a second section located adjacent to a respective central portion, said measuring portions of said arms being so curved that in said initial position the first and second section of each measuring arm are located at opposite sides of said longitudinal axis, the first sections of said measuring portions are located at opposite sides of said longitudinal axis, and the second sections of said measuring portions are also located at opposite sides of said longitudinal axis.

7. An instrument as defined in claim 3, wherein each of said loops is flattened and has a smaller dimension measured in a plane which is normal to said measuring portions, and a greater dimension which is measured in a plane which is substantially parallel to said measuring portions.

8. An instrument as defined in claim 1, wherein said loops are constructed of an expansible material.

9. An instrument as defined in claim 1, wherein each of said loops is split and constructed of a springy material.

10. An instrument as defined in claim 1, wherein said end of said one indicating portion which is provided with said scale is formed as a sector having rounded outer edges.

11. An instrument as defined in claim 1, wherein each said loops has an inner opening which is conical and converges in said first direction.

12. A method of measuring dilatation of cervix uteri during a first stage of labor, comprising the steps of
providing an instrument having two arms which are connected with one another in a scissors-like manner and having two measuring portions of differing lengths provided with expansible loops and two indicating portions one of which is provided with a scale with graduation marks whereas the other indicating portion has an indicating tip;
moving said arms toward one another so that said loops are located one after the other and coaxial with one another;
inserting a finger of a user simultaneously into two thus-located loops so that it extends outwardly beyond the latter to palpate an edge of an orifice of cervix uteri;
moving said arms away from one another so that said loops are spaced from one another;
inserting two fingers each in one of the thus-spaced loops so that the fingers extend outwardly beyond the same to palpate the edge of the orifice of cervix uteri;
reading a graduation marks to which said indicating tip points after each of said inserting steps; and
performing said inserting steps with expanding of said expansible loops when the user's fingers are thicker than the latter.

* * * * *